United States Patent
Glukhovsky

(10) Patent No.: US 7,245,954 B2
(45) Date of Patent: Jul. 17, 2007

(54) MEASURING A GRADIENT IN-VIVO

(75) Inventor: Arkady Glukhovsky, Santa Clarita, CA (US)

(73) Assignee: Given Imaging Ltd., Yoqneam (IL)

( * ) Notice: Subject to any disclaimer, the term of this patent is extended or adjusted under 35 U.S.C. 154(b) by 329 days.

(21) Appl. No.: 10/808,573

(22) Filed: Mar. 25, 2004

(65) Prior Publication Data

US 2004/0193029 A1    Sep. 30, 2004

Related U.S. Application Data

(60) Provisional application No. 60/457,594, filed on Mar. 27, 2003.

(51) Int. Cl.
*A61B 5/00* (2006.01)
(52) U.S. Cl. ...................... 600/350; 600/345
(58) Field of Classification Search ................ 600/345, 600/350, 361, 424
See application file for complete search history.

(56) References Cited

U.S. PATENT DOCUMENTS

| | | | |
|---|---|---|---|
| 3,682,160 A * | 8/1972 | Murata | ....................... 600/302 |
| 3,683,389 A | 8/1972 | Hollis | |
| 3,971,362 A | 7/1976 | Pope et al. | |
| 4,200,110 A * | 4/1980 | Peterson et al. | ............ 600/367 |
| 4,278,077 A | 7/1981 | Mizumoto | |
| 4,689,621 A | 8/1987 | Kleinberg | |
| 4,741,327 A | 5/1988 | Yabe | |
| 4,844,076 A | 7/1989 | Lesho et al. | |
| 5,279,607 A | 1/1994 | Schentag et al. | |
| 5,604,531 A | 2/1997 | Iddan et al. | |
| 5,819,736 A | 10/1998 | Avny et al. | |
| 5,833,603 A | 11/1998 | Kovacs et al. | |
| 5,853,005 A | 12/1998 | Scanlon | |
| 6,074,349 A | 6/2000 | Crowley | |
| 6,165,128 A | 12/2000 | Céspedes et al. | |
| 6,240,312 B1 | 5/2001 | Alfano et al. | |
| 6,285,897 B1 * | 9/2001 | Kilcoyne et al. | ........... 600/350 |
| 6,475,145 B1 | 11/2002 | Baylor | |
| 6,584,348 B2 | 6/2003 | Glukhovsky | |
| 6,607,301 B1 | 8/2003 | Glukhovsky et al. | |

(Continued)

FOREIGN PATENT DOCUMENTS

DE    34 40 177    5/1986

(Continued)

OTHER PUBLICATIONS

U.S. Appl. No. 10/724,109, filed Dec. 1, 2003, Glukhovsky et al.

(Continued)

*Primary Examiner*—Charles A. Marmor, II
*Assistant Examiner*—Karen E Toth
(74) *Attorney, Agent, or Firm*—Pearl Cohen Zedek Latzer LLP

(57) ABSTRACT

A device, system and method for in-vivo sensing (e.g., pH sensing, pressure sensing, or other sensing) may include more than one sensor receiving in-vivo data. The sensed data may be analyzed to, for example, determine a gradient or fluid flow. A device including multiple sensors may be held or immobilized in-vivo, and may detect a fluid flow or gradient moving past the sensors.

15 Claims, 6 Drawing Sheets

U.S. PATENT DOCUMENTS

| | | |
|---|---|---|
| 2001/0017649 A1 | 8/2001 | Yaron |
| 2001/0051766 A1 | 12/2001 | Gazdzinski |
| 2002/0109774 A1* | 8/2002 | Meron et al. ................. 348/74 |
| 2002/0151816 A1* | 10/2002 | Rich et al. ................. 600/547 |
| 2002/0198439 A1 | 12/2002 | Mizuno |
| 2003/0018280 A1 | 1/2003 | Lewkowicz et al. |
| 2003/0040685 A1 | 2/2003 | Lewkowicz et al. |
| 2003/0195415 A1 | 10/2003 | Iddan |
| 2004/0158138 A1* | 8/2004 | Kilcoyne et al. ........... 600/350 |

FOREIGN PATENT DOCUMENTS

| | | |
|---|---|---|
| JP | 57-45833 | 3/1982 |
| JP | HEI 3-289779 | 12/1991 |
| JP | 4109927 | 4/1992 |
| JP | HEI 4-109927 | 4/1992 |
| JP | HEI 4-180736 | 6/1992 |
| JP | 5015515 | 1/1993 |
| JP | 2001224553 | 8/2001 |
| WO | WO 00/22975 | 4/2000 |
| WO | WO 01/08548 | 2/2001 |
| WO | WO 01/50941 | 7/2001 |
| WO | WO 02/26103 | 4/2002 |
| WO | WO 02/094337 | 11/2002 |
| WO | WO 2004/004540 | 1/2004 |

OTHER PUBLICATIONS

Roubik, et al., "Reference Microelectrodes Design Evaluation for On-Chip ISFET-Based Microsensors for "in vivo" Blood Measurements".

"Chemical Microsystem", Department of Microelectronics, Faculty of Electrical Engineering Czech Technical University in Prague, Technická 2, CZ-166 27 Prague 6, Czech Republic.

F. Vald's-Perezgasga, et al., "Isfet Applications in Biological Matter: An Overview", downloaded Oct. 27, 2002, www.cinstrum.unam.mx/revista/pdtv4n3/art3.PDF.

Wireless transmission of a color television moving image from the stomach using a miniature CCD camera, light source and microwave transmitter. Swain CP, Gong F, Mills TN. Gastrointest Endosc 1997;45:AB40.

Robots for the future—Shin-ichi, et al, Nov. 29, 2001.

The Radio Pill, Rowlands, et al., British Communications and Electronics, Aug. 1960, pp. 598-601.

Video Camera to "TAKE"—RF System lab, Dec. 25, 2001.

www.oceanoptics.com—pH Sensor & Accessories, © 2001.

Wang, et al., "Integrated Micro-Instrumentation for Dynamic Monitoring of the Gastro-Intestinal Tract", Presented at IEEE Instrumentation and Measurement Technology Conference, May 2002, Anchorage, Ak, USA, www.see.ed.ac.uk/Naa.publications.html.

* cited by examiner

MEASURING A GRADIENT IN-VIVO

CROSS-REFERENCE TO RELATED APPLICATIONS

This application claims the benefit from prior U.S. provisional application Ser. No. 60/457,594, filed on Mar. 27, 2003 entitled "MEASURING A GRADIENT IN VIVO", which is incorporated in its entirety by reference herein.

FIELD OF THE INVENTION

The present invention relates to measurement of a static or dynamic gradient in a body lumen, for example, to measurement of a pH gradient in the esophagus.

BACKGROUND OF THE INVENTION

Gastroesophageal reflux occurs when stomach acid intermittently surges into the esophagus. It is common for most people to experience this acid reflux occasionally as heartburn. Gastroesophageal reflux disease (GERD) is a clinical condition in which the reflux of stomach acid into the esophagus is frequent enough and severe enough to impact a patient's normal functioning or to cause damage to the esophagus. GERD is sometimes also referred to as "reflux" or "reflux esophagitis".

In known methods for gastroesophageal reflux monitoring a pH sensing device is held in the lower esophagus and the pH levels therein are monitored for a period of time (usually 24–48 hours). The device may be attached to the esophageal wall or it may be suspended in the esophagus from an extension (e.g. catheter or cord). The known methods for in-vivo pH monitoring, specifically for gastroesophageal reflux monitoring, typically measure pH prevailing in a body lumen, such as the esophagus, however they usually do not measure other parameters of a pH reflux, such as pH gradient.

SUMMARY OF THE INVENTION

According to an embodiment of the present invention, there is provided a device, system and method for measuring in-vivo gradients. In one embodiment of the invention, the device may include two sensors (more than two sensors may be used) separated by a distance D from each other. In an exemplary embodiment, the device may be an in-vivo device and the sensors may be pH sensors that may, for example, measure pH in, for example, the esophagus. In one embodiment of the invention, the output for the two sensors may be processed to obtain a measure of gradient. In another embodiment of the invention, the device may include a transmitter that may transmit output to an external recorder.

BRIEF DESCRIPTION OF THE DRAWINGS

The present invention will be understood and appreciated more fully from the following detailed description taken in conjunction with the drawings in which.

Figure 1A:
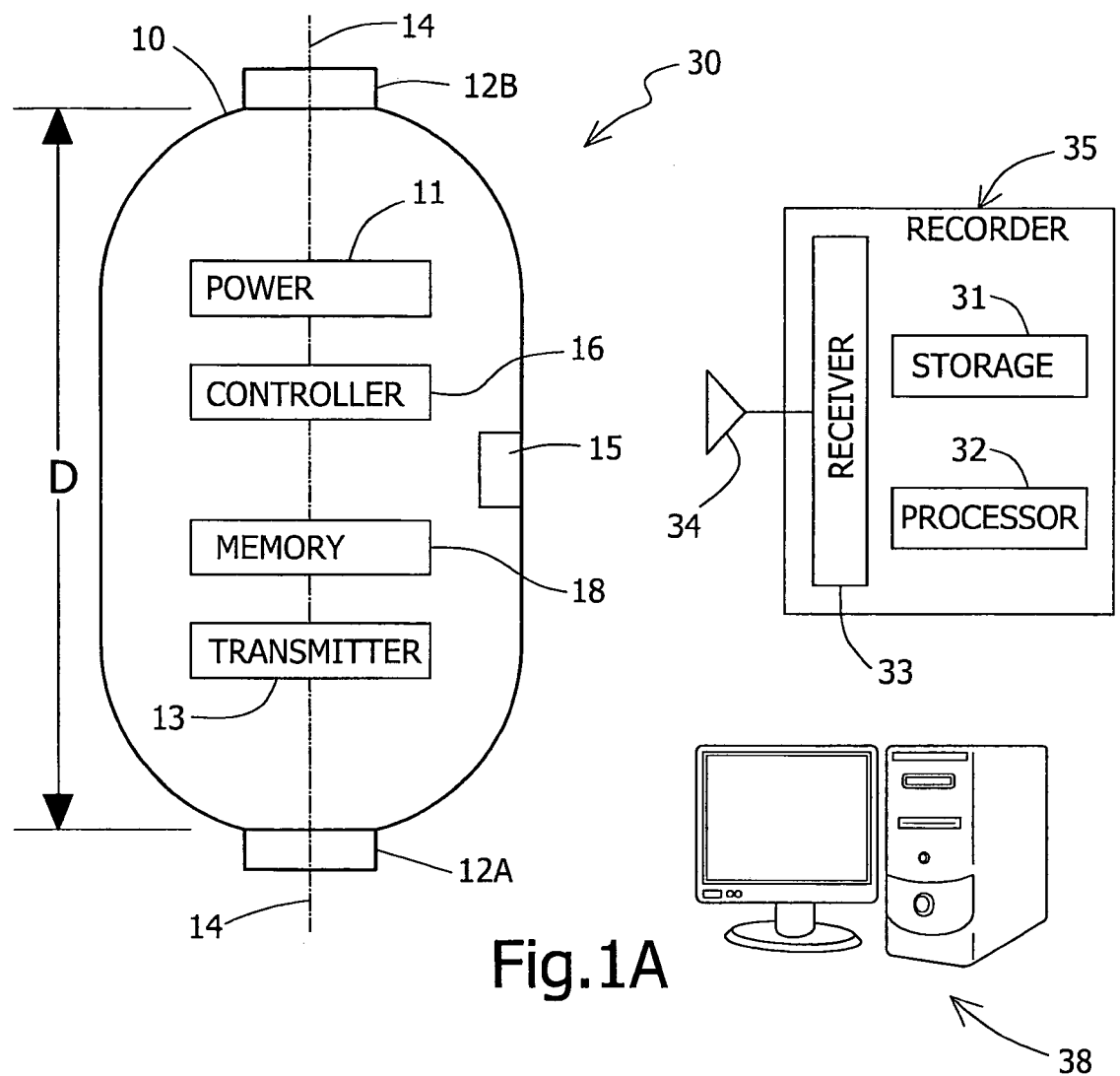
FIG. 1A is a schematic illustration of a device according to an embodiment of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Reference is now made to FIG. 1A, which schematically illustrates a system according to an embodiment of the invention. The system 30 includes an in-vivo device 10 and a recorder 35. The device 10 may include two or more comparable sensors, for example, two pH sensors 12A and 12B that may be separated by a distance D and a controller or processor 16 that may be connected to pH sensors 12A and 12B. In other embodiments of the invention, a processor may not be included in the device 10. The sensors may sense in modes other than pH, such as, for example, pressure, electrical conductivity or resistance, light, blood, oximetry, etc. The device 10 may include additional sensors, and in addition may include imaging capability. The device 10 may include, for example, a transmitter 13 for transmitting data to an external receiving unit 35. The transmitter 13 or another component may sample data output from sensors within the device 10, and then transmit the data, possibly to an external device. The transmitter 13 may be for example an ultra low power RF transmitter. In one embodiment of the invention, the transmitter 13 may be for example provided in chip scale packaging. Other suitable transmitters may be used. Transmitter 13 may include processing or control capability, for example, processor 16 or its functionality may be included in transmitter 13, and transmitter 13 may act as a controller. The transmitted data may be, for example, output from a sensor, for example one or more pH sensors or output of processor 16, which may, for example, analyze, compare or otherwise integrate several sensor (e.g., pH) measurements. Typically, a processor or controller analyzing sensor data is external to device 10, but in other embodiments need not be. Data may be transmitted from transmitter 13 by for example, radio frequency, ultrasonic link, or via wired link—e.g. wire, optical fiber, etc. In alternate embodiments data may be transmitted, for example, directly from the pH sensing sensors 12 or the data may be recorded onto a memory, for example, a memory on processor 16, or a separate memory unit (not shown), to be retreated at a later time, for example, after the device 10 is recovered from a patient's body, or after the device 10 has competed recording measurements. According to some embodiments, the device 10 may include a power supply unit 11 for providing power to the elements of the device 10. Power supply unit 11 may include for example one or more suitable batteries. Some examples of suitable batteries may include a silver oxide battery, a lithium battery; in an alternative embodiment power may be delivered into the device 10 from an external source by a wireless method. According to some embodiments the processor 16 may be a separate unit, possibly positioned out side a patient's body. Data from sensors 12A and/or B may be transmitted to an external receiver/recorder 35, for example, worn by the patient for recording and storage. According to one embodiment the receiver/recorder 35 may include a storage unit 31, an optional controller or processing unit 32, a receiver 33 and one or more antennas 34. Antenna 34 may be worn on the body, for example, on or near the neck or throat so that signals, for example, from the esophagus, may be picked up easily. The antenna 34 may be worn, or positioned in other locations or may be imbedded in the recorder 35. Recorder 35 may also include for example, an amplifier, light indicator, or display, such as an LCD or other suitable display to present output of the in-vivo device 10 or analyzed data to a user. The output may be for example, visual audio or both. Other methods of presentation may be used or data recorded in recorder 35 may be downloaded to a processing unit 38 such as for example a computer, or other processing units for processing and/or displaying output.

Device 10 may be for example, a capsule or other unit where all the components are substantially contained within a container or shell, and where the device does not require any wires or cables to, for example, receive power or transmit information. In one embodiment of the invention, the capsule may be a swallowable capsule or other device that naturally traverses the GI tract while measuring, in-vivo gradients. The device may be autonomous. Device 10 need not be a capsule, and may include other configurations.

FIG. 1A shows two sensors, 12A and 12B. Sensors 12A and 12B may be any suitable type of sensor such as a pH sensor. PH sensors may include, for example, electrodes, ion selective field effect transistors (ISFET), pH sensitive color indicators, and so on, as is known in the art; other suitable pH sensors may be used. For example, pH sensitive electrodes may include an external ring 120 (FIG. 2A) or cylindrical electrode 125A and 125B (FIG. 2B) made of antimony and a zinc-silver chloride electrode. A saline solution such as for example, a 0.9% physiologic saline solution may be introduced into the electrode. A potential difference, which develops between the two electrodes is pH dependent, and may be applied to an amplifier and further processed by known hardware/software methods. Typically, the device includes two or more sensors that sense in the same modality or sense the same type of data (e.g., two or more sensors each sensing pH, each sensing pressure, etc.) Thus, according to one embodiment, sensors 12A and 12B each sense the same type of data.

The pH sensors 12A and 12B output is typically conveyed to processor 16. Output from processor 16 may then be conveyed to a memory unit 18 or to transmitter 13 for being transmitted to an external receiving unit (not shown). Data may be conveyed through wired connections in device 10 or wirelessly, for example by RF or any other suitable wireless connection. The connections between elements within the device 10 are not shown so as not to obscure the figure. In an alternate embodiment processing may be performed externally to the device 10, such as in processing unit 32 or 38.

Sensors 12A and 12B may be placed in any appropriate location on device 10. FIG. 1A shows them at both ends; however, they may be placed anywhere on device 10 as long as there is a distance D, possibly along an axis, e.g., longitudinal axis 14 of device 10, between the sensors 12A and 12B. According to one embodiment two pairs of electrodes are located along the longitudinal axis of the device. According to another embodiment more than two pairs of electrodes may be located along the device other than on the longitudinal axis. Other numbers of sensors may be used, and need not be paired. Sensors 12A and 12B or other sensors may be placed on a device that is not elongated (e.g., round, square).

Figure 1B:
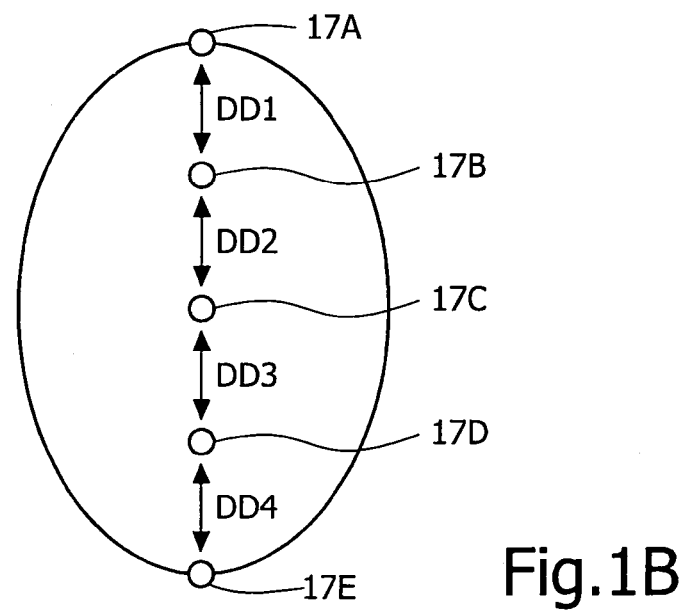
FIG. 1B is a schematic illustration of a device according to an embodiment of the invention.

Reference is now made to FIG. 1B showing schematically a device according to another embodiment of the present invention. The device 20 may include an array of sensors, for example, 17A–17E, with distances DD1–DD4, between 17A–17B, 17B–17C, 17C–17D, 17D–17E, respectively. Sensors 17A–17E may be a single type of sensor, or alternatively more than one type of sensor. Although, in FIG. 1B sensors 17A–17E, are shown to be evenly distributed along device 20, in alternate embodiments other forms of distribution may be used.

Data transmitted to an external receiving unit may be recorded and/or presented to an operator in any suitable way, such as graphically, for example, on a screen of a workstation. Other ways of presenting transmitted data are possible, such a number, an audio signal, a flashing light etc.

Figure 2A:
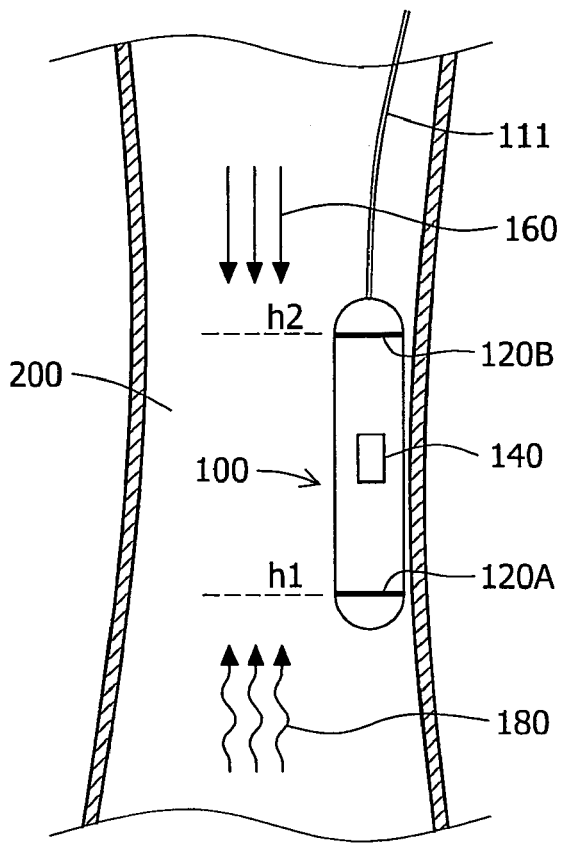
FIGS. 2A, 2B and 2C are schematic illustrations of devices, constructed and operative in accordance with embodiments of the present invention.

Reference is now made to FIG. 2A, which illustrates a device, constructed and operative in accordance with an embodiment of the present invention. The device 100 may be, for example, capsule or rod shaped, but other suitable shapes or configurations may be used. Device 100 may include sensors 120A and 120B, such as pH sensors, a processor 140, a transmitter (not shown) and a power source (not shown). Alternatively, data may be transmitted through a wired connection (e.g., cord 111) and/or power may be supplied to the electrical elements of the device 100 through a wired connection (e.g., cord 111). According to some embodiments the device 100 may include an additional sensor 15, such as pressure, temperature, image sensors, blood sensor, or oximetry sensor. For example, device 100 may include an image sensor in an embodiment which may be similar to embodiments described in U.S. Pat. No. 5,604,531 to Iddan et al., and/or WO 01/65995, entitled "A Device And System For In Vivo Imaging", published on 13 Sep. 2001, both of which are assigned to the common assignee of the present invention and which are hereby incorporated by reference.

Unlike prior art devices, which typically may have a single pH sensor; embodiments of the present invention may have multiple pH sensors, each separately measuring the pH, optionally at separate locations within a body lumen. According to one embodiment devices 10, 20, or 100 may measure the pH gradient of a fluid flowing past the device. While the functionality in a specific setting is described with respect to device 100, such functionality may also be performed by system 30, device 20, or other embodiments described herein. The fluid may include food 160, which has been swallowed, or reflux 180 that surges into esophagus 200 from the stomach. According to other embodiments measurement of for example blood flow (e.g., velocity) may be based on detecting pressure gradients during the cardiac cycle. Additionally, the flow of urine may be monitored. According to these embodiments a device, such as a capsule (s) may include pressure or other suitable transducers.

Processor 140 may process the sensed data from sensors 120A and 120B, for example, to determine the gradient and speed of fluid flow, and possibly other parameters such as direction. If the fluid is reflux, as may be determined, for example, by the direction of flow, processor 140 may also determine a rough estimate of the distance covered by the reflux. For example, if a sensor 120A, which is positioned closer to the stomach, sensed a pH indicative of a reflux but a sensor 120B, which is positioned further from the stomach, did not, then processor 140 may determine that the reflux reached a distance between the two sensors (i.e. that the reflux was higher than location h1 of sensor 120A but lower than location h2 of sensor 120B).

Moreover, other parameters may be sampled and included in the processing to present a more complete picture of the reflux event. For example, processor 140 may record times of ingestion, e.g. identified by a fluid flow in a direction towards the stomach as determined by the gradient measurements obtained with sensors 120A and 120B. Additional information may be integrated as well, for example, images taken by an image sensor in device 100 or, pressure and/or temperature measurements taken by appropriate sensors in device 100. According to alternate embodiments, different data may be transmitted to an external receiving/processing unit for integration to be performed externally.

Device 100 may be positioned in a body lumen such that at least two pH sensors 120A and 120B may measure a pH gradient within the body lumen. Devices 10, 20 or 100 may be positioned within the GI tract, for example for measuring pH gradients within the esophagus, stomach, small intestine, large intestine or other parts of the GI tract. Alternately, devices 10, 20, or 100 may be positioned within other body lumens such as blood vessels, the urinary tract, the reproductive tract and others. According to one embodiment the devices 10, 20, or 100 may be positioned in a body lumen and held in place by an external device such as an endoscope, catheter, needle, stent, etc., for example, as known in the art. In one embodiment of the invention, device 10, 20, or 100 may be an integral part of an external device, for example, an endoscope, catheter, needle, stent, etc. According to another embodiment the devices 10, 20, or 100 may be transiently attached to a body lumen wall by an attachment mechanism, for example, by use of vacuum, clips, suturing, elastic band, etc., for example, as is known in the art.

Figure 2B:
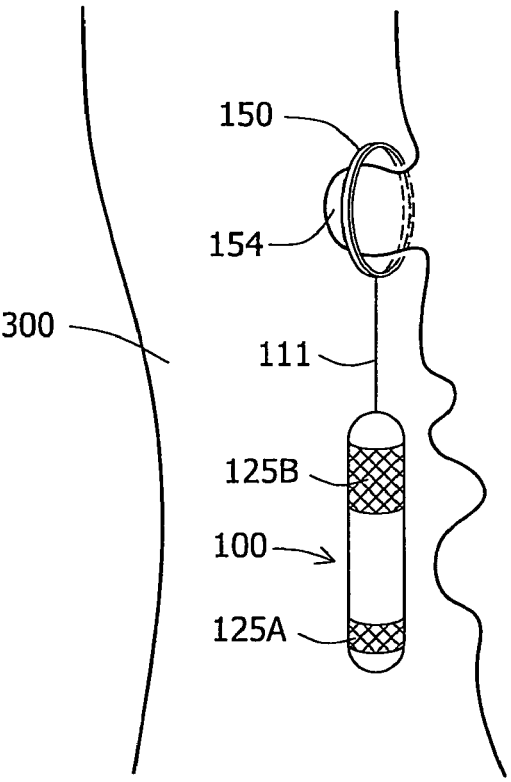

An embodiment of the present invention may be configured for being immobilized or held in-vivo. For example, a device may include a shell or container configured for being immobilized, including recesses which may be tied or otherwise connected to in-vivo tissue, including clamps, pins, etc. A device may be attached to a cord or band from which it is hung from a relatively stationary position in-vivo, for example within the esophagus, or which may be tied to connected to an in-vivo site. Reference is now made to FIG. 2B in which device 100 (or devices 10 or 20) is attached to the wall of a body lumen 300 (such as a section of the GI tract) with an elastic band 150 or other suitable extension or cord which, in turn, is placed around a protuberance 154 in the wall of the body lumen 300. Device 100 then hangs down into the body lumen 300 and measures the pH over a pre-defined period of time, such as, for example, 24 hours. Other suitable time periods may be used. Other known methods for positioning and immobilizing a device to a body lumen wall may be used in accordance with embodiments of the invention and other body lumens besides the esophagus may be sensed. Examples of devices which may be immobilized or which are configured to be immobilized in-vivo, and some systems and methods for immobilizing a device in-vivo are described in WO 02/26103 published on Apr. 4, 2002, and published application US-2002-0042562-A1, which are assigned to the common assignee of the present invention and which are hereby incorporated by reference. Other systems and method of immobilizing an in-vivo device may be used.

Figure 2C:
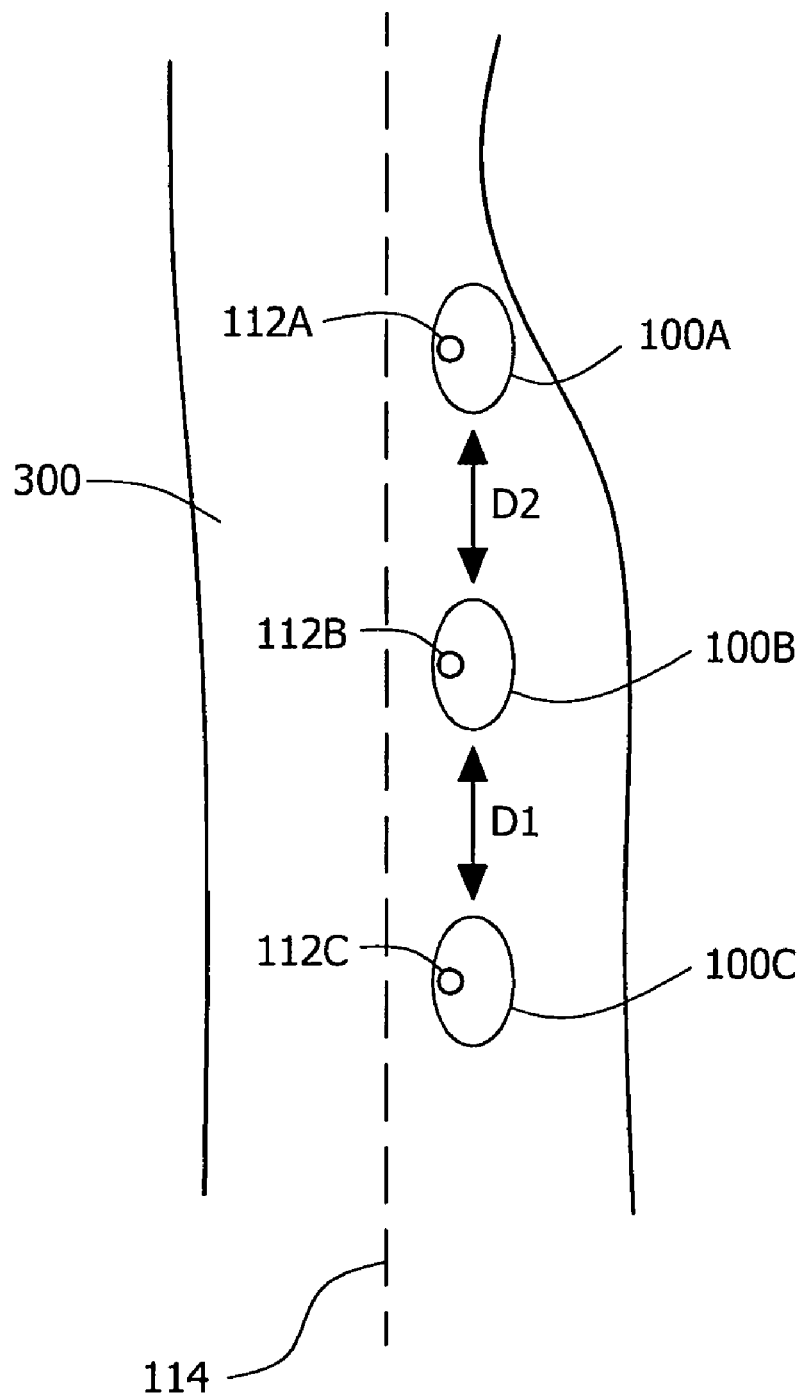

Reference is now made to FIG. 2C in which a plurality of devices 100A, 100B, and 100C are shown (similarly, devices 10 and 20 may be used in multiple device systems as well). According to an embodiment of the invention each of the devices may include a sensor, such as sensors 112A, 112B and 112C. The devices 100A, 100B, and 100C are distanced from each other by distances D1 and D2 and are attached to a body lumen 300 wall along an axis 114 of the body lumen. The devices may be connected to each other or they may each separately transmit data (for example as described herein) to an external receiving unit. Data received from the distanced devices may be used to calculate parameters of a gradient prevalent in the body lumen 300. For example, at least two of the sensors 112A, 112B or 112C may be pH, temperature or pressure sensors and thus they may monitor a pH, temperature or pressure gradient occurring along axis 114 of body lumen 300. According to other embodiments other numbers and types of sensors may be used.

Figure 3A:
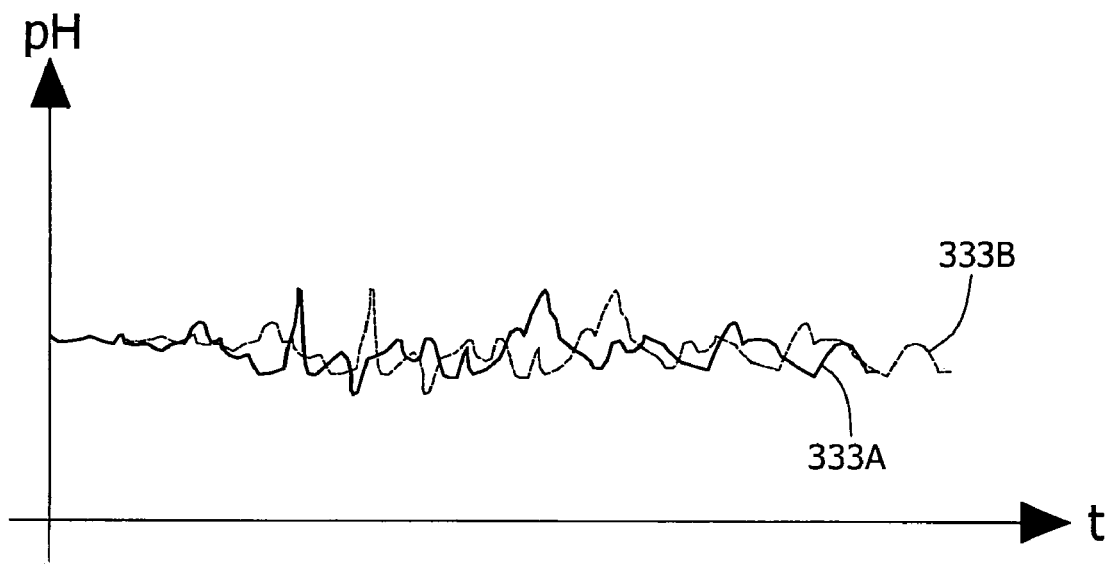
FIG. 3A is a graphical illustration of exemplary output of pH sensors according to embodiments of the present invention.
Figure 3B:
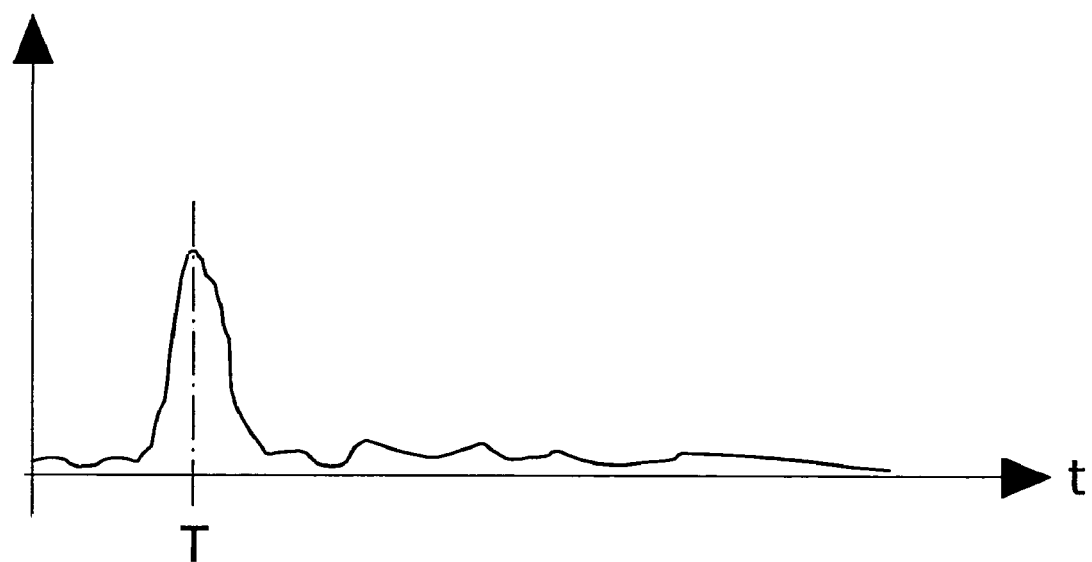
FIG. 3B is a graphical illustration of an exemplary correlation of the output of pH sensors according to embodiments of the present invention.

Reference is now made to FIGS. 3A and 3B, which illustrate exemplary output from multiple sensors, for example, from sensors 12A and 12B, respectively (or other sensor described herein, such as sensors 17A–D, 120, 125, 112A–C, etc.), and their cross correlation, respectively, over time. FIG. 3A shows an exemplary output of sensors 12A and 12B, where the output from sensor 12A is shown with a solid line 333A and that from sensor 12B is shown with a dashed line 333B. In the example of FIG. 3A, the outputs are shifted from each other by a time period T. FIG. 3B shows the cross-correlation between the output of the two sensors 12A and 12B. According to one embodiment a device according to an embodiment of the invention may be positioned within a flow of a fluid passing through, for example, the esophagus. The multiple sensors may detect for example a fluid flow or gradient moving past the sensors. Sensors may measure in a mode such as for example pH in two or more different locations. In an exemplary embodiment the output of the two sensors 12A and 12B may correspond, for example with the outputs shown in FIG. 3A that may be shifted by a time T. A positive dynamic gradient may be expressed when, for example, the solid line is shifted forward in time by an amount T. Such determination may be made, for example, by matching portions of the signal stream received. Thus, the fluid has moved from one sensor to the next (i.e. the distance D) in the time T. In other words, the velocity (V) of the fluid may be expressed by the following relationship:

$$V = D/T$$

and its direction may be positive, from sensor 12A to sensor 12B. This positive dynamic gradient may indicate reflux. A negative dynamic gradient may indicate ingestion of food, or retraction of the reflux back to the stomach. A dynamic gradient may be defined as a gradient that may change quickly with time. A static gradient may be defined as a gradient that may be relatively constant with time, for example the natural gradient in pH between the relatively neutral pH in the esophagus and the relatively acid condition in the stomach, may be considered a static gradient.

In accordance with an embodiment of the present invention, processor 16 may used to determine the presence and possibly direction of fluid flow with, for example, a comparator. PH sensor outputs, or other sensor outputs may change with the introduction of fluid flow or movement, due to, for example, the acidity level of the fluid. In one embodiment, a fluid may be determined to be present if the output of at least one sensor 12 is greater than a threshold. For example, if the pH determined at a sensor changes, it may be determined that fluid has moved past the sensor. If the output of the cross-correlation operation is not above a threshold, then processor 16 may determine that the fluid passed only one sensor and did not reach the second or other sensors.

Presumably, the higher the speed of the reflux at a given location, the higher it may reach in the esophagus and the more severe the reflux may be.

Figure 4A:
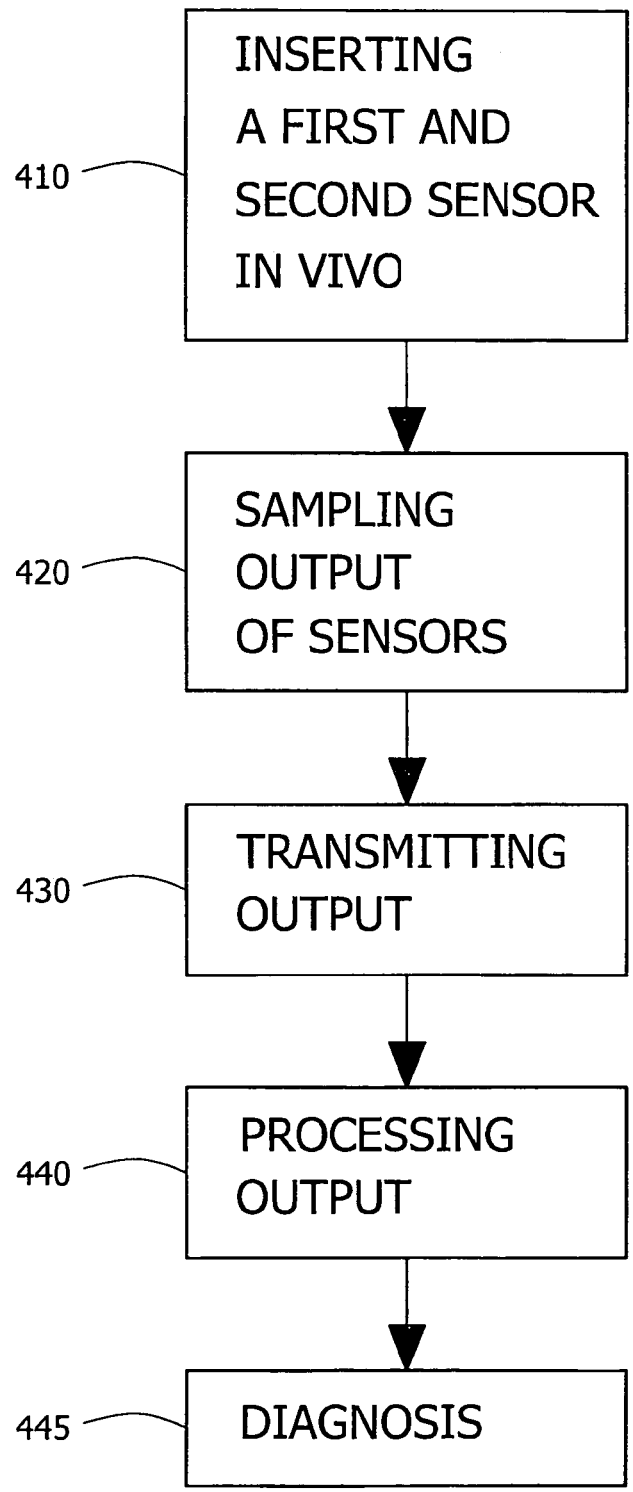
FIGS. 4A and 4B are a flow charts describing a method for measuring a gradient in-vivo according to an embodiment of the present invention.

Reference is now made to FIG. 4A showing an exemplary flow chart describing a method for measuring a gradient in-vivo according to an embodiment of the present invention. In block 410 a first and second sensor may be inserted in-vivo at a distance D between them. in other embodiments of the present invention, more than two sensors may be used and more than one gradient may be determined. In one exemplary embodiment, the first and second sensor may be pH sensors inserted into the esophagus or swallowed. In other embodiments, the sensors may other sensors or may be inserted in other body lumens such as blood vessels, urinary tact, reproductive tract, etc. The sensors typically sense in the same modality or sense the same type of data, and in one embodiment are included in the same physical device or package (e.g., a capsule). However, the two sensors may sense in different modalities and/or may be located in different devices or packages. Subsequently, in block 420 the sensors may sample in-vivo conditions. In block 430, the sampled output of the sensors may be transmitted to an external receiver/recorder. The data may be transmitted and/or downloaded or otherwise communicated to the processor, which may accept or receive the data from the sensors. In block 440, the output may be processed. In block 445 diagnosis based on the output may be performed. The diagnosis may involve, for example, comparing data from different sensors, performing a cross correlation, etc. A diagnosis may include, for example, a determination of a fluid-flow, which may include in addition a direction, speed, gradient, or other information on the fluid flow. In an alternate embodiment, the output may be processed or partially processed in-vivo prior to transmission. In the case that the processor or controller is in the same device as the sensors, the data may be simply communicated using, e.g., a wire or an intermediate device. Transmission may be for example by wire or by wireless transmission. Other operations and series of operations may be used.

Figure 4B:
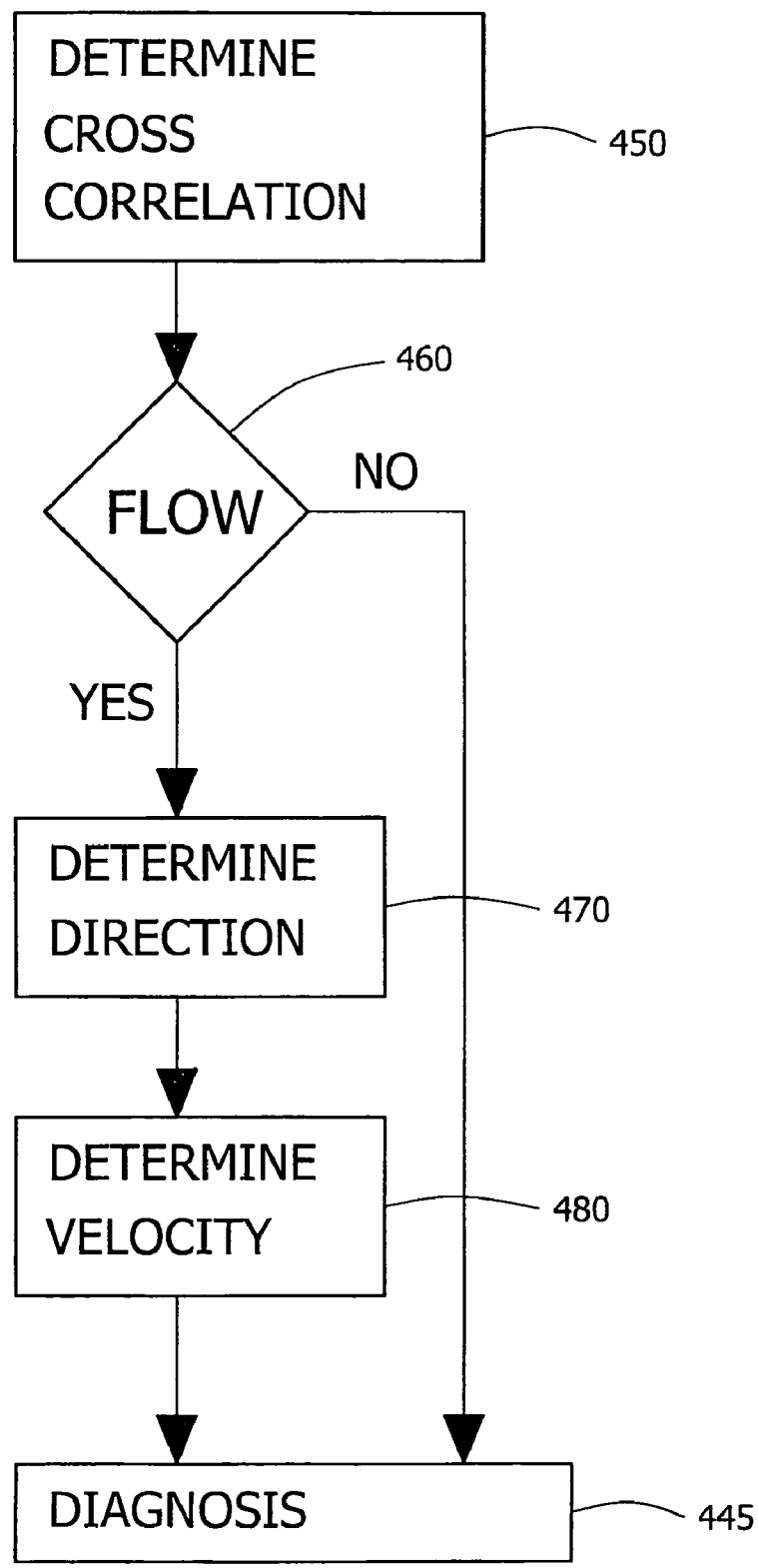

FIG. 4B shows an exemplary flow chart describing a processing output and diagnosis procedure according to one embodiment. In block 450, the output of the sensors may be compared so as to determine the cross correlation between the output of the sensors. Other suitable comparisons of data may be performed. Based on analysis of the comparison between the output of the sensors and the cross correlation, as for example is described herein, flow may be detected (460). In a case where flow is detected, the direction of the flow (470) and velocity of the flow (480) may be determined. Based on the determinations made and possibly other suitable parameters, in-vivo conditions such as for example, GERD, may be determined. Other operations and series of operations may be used.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method for determining a direction of flow through a gastrointestinal tract, the method comprising:
    inserting first and second pH sensors within the gastrointestinal tract, the first and second pH sensors separated by a distance D;
    sampling an output of the first and second pH sensors over time;
    determining a gradient between the output of the first and second pH sensors over time; and
    determining the direction of flow over the distance D based on the gradient.

2. The method according to claim 1 comprising immobilizing the first and the second pH sensors in the gastrointestinal tract.

3. The method according to claim 1 comprising immobilizing the first and the second pH sensors in an esophagus.

4. The method according to claim 1 wherein the first and the second pH sensors are comprised within a swallowable capsule.

5. The method according to claim 1 comprising transmitting the output of the first and the second pH sensors to an external receiver.

6. The method according to claim 1 comprising transmitting the determined direction of flow to an external receiver.

7. The method according to claim 1 comprising diagnosing GERD based on output of the first and the second pH sensors.

8. The method according to claim 1 comprising determining the velocity of flow over the distance D based on the output of the first and second pH sensors.

9. A system for determining a direction of flow through a gastrointestinal tract, the system comprising:
    first and second pH sensors configured to be inserted within the gastrointestinal tract, the pH sensors separated by a distance D; and
    a processor configured to determine a direction of flow over the distance D based on a gradient between an output of the first and second pH sensors over time.

10. The system according to claim 9 wherein the first and second pH sensors are configured to be immobilized in an esophagus.

11. The system according to claim 9 wherein the first and second pH sensors are comprised within a swallowable capsule.

12. The system according to claim 11 wherein the swallowable capsule comprises an image sensor.

13. The system according to claim 9 wherein the first and second pH sensors comprise ion selective field effect transistors.

14. The system according to claim 9 wherein the first and second pH sensors comprise pH sensitive color indicators.

15. The system according to claim 9 comprising a transmitter configured to transmit the output of the first and second pH sensors to an external receiver.

* * * * *